United States Patent [19]
Eisenschmid et al.

[11] Patent Number: 5,886,236
[45] Date of Patent: Mar. 23, 1999

[54] PROCESS FOR PRODUCING ALDEHYDE ACID SALTS

[75] Inventors: Thomas Carl Eisenschmid, Cross Lanes; John Robert Briggs, Charleston; Diane Lee Packett, South Charleston; Kurt Damar Olson, Cross Lanes; John Michael Maher, Charleston, all of W. Va.

[73] Assignee: Union Carbide Chemicals & Plastics Technology Corporation, Danbury, Conn.

[21] Appl. No.: 834,248

[22] Filed: Apr. 15, 1997

[51] Int. Cl.⁶ .................................................. C07C 45/50
[52] U.S. Cl. ........................... 568/454; 568/451; 560/207
[58] Field of Search .................................... 568/454, 451; 560/207

[56] References Cited

U.S. PATENT DOCUMENTS

| | | | |
|---|---|---|---|
| 3,485,821 | 12/1969 | Sheehan | 260/239.3 |
| 3,652,549 | 3/1972 | Fujita et al. | 260/239.3 |
| 4,101,588 | 7/1978 | Nienburg et al. | 260/604 |
| 4,550,195 | 10/1985 | Platz ert al. | 560/206 |
| 4,586,987 | 5/1986 | Schneider et al. | 560/206 |
| 4,622,423 | 11/1986 | Burke | 562/522 |
| 4,730,040 | 3/1988 | Vagt et al. | 540/538 |
| 4,730,041 | 3/1988 | Hutmacher et al. | 540/538 |
| 4,731,445 | 3/1988 | Hutmacher et al. | 540/538 |
| 4,801,738 | 1/1989 | Schneider et al. | 560/177 |
| 4,824,817 | 4/1989 | Drent | 502/154 |
| 4,879,405 | 11/1989 | Naeumann et al. | 560/211 |
| 4,894,474 | 1/1990 | Maerkl et al. | 560/206 |
| 4,910,328 | 3/1990 | Bertleff et al. | 560/177 |
| 4,925,972 | 5/1990 | Maerkl et al. | 560/206 |
| 4,933,487 | 6/1990 | Hoelderich et al. | 560/205 |
| 5,003,102 | 3/1991 | Bertleff et al. | 560/177 |
| 5,026,901 | 6/1991 | D'Amodre | 560/207 |
| 5,028,734 | 7/1991 | Drent | 560/207 |
| 5,041,642 | 8/1991 | Jenck | 562/522 |
| 5,068,398 | 11/1991 | Merger et al. | 560/156 |
| 5,145,995 | 9/1992 | Burke | 562/522 |
| 5,159,107 | 10/1992 | Panitz et al. | 560/206 |
| 5,198,577 | 3/1993 | Denis et al. | 562/522 |
| 5,250,726 | 10/1993 | Burke | 562/522 |
| 5,264,616 | 11/1993 | Roeper et al. | 560/175 |
| 5,288,903 | 2/1994 | Bunel et al. | 562/598 |
| 5,292,944 | 3/1994 | Atadan et al. | 562/590 |
| 5,312,979 | 5/1994 | Denis et al. | 562/522 |
| 5,312,996 | 5/1994 | Packett | 568/454 |
| 5,495,041 | 2/1996 | Sielcken et al. | 560/207 |
| 5,710,344 | 1/1998 | Breikss | 568/454 |

FOREIGN PATENT DOCUMENTS

| | | |
|---|---|---|
| 0556681 | 2/1903 | European Pat. Off. . |
| 0271145 | 11/1987 | European Pat. Off. . |
| 0273489 | 6/1988 | European Pat. Off. . |
| 0405433 | 1/1991 | European Pat. Off. . |
| 0562450 | 3/1993 | European Pat. Off. . |
| 0577205 | 6/1993 | European Pat. Off. . |
| 0643031 | 8/1994 | European Pat. Off. . |
| 0648731 | 4/1995 | European Pat. Off. . |
| 0662468 | 7/1995 | European Pat. Off. . |
| 0712828 | 11/1995 | European Pat. Off. . |
| 0728732 | 8/1996 | European Pat. Off. . |
| 0729943 | 9/1996 | European Pat. Off. . |
| 0729944 | 9/1996 | European Pat. Off. . |
| 6306012 | 4/1993 | Japan . |
| 9426688 | 11/1994 | WIPO . |
| 9506025 | 3/1995 | WIPO . |
| 9506027 | 3/1995 | WIPO . |
| 9518089 | 7/1995 | WIPO . |
| 9518783 | 7/1995 | WIPO . |
| 9530680 | 11/1995 | WIPO . |
| 9616923 | 6/1996 | WIPO . |
| 9617817 | 6/1996 | WIPO . |
| 9702091 | 1/1997 | WIPO . |
| 9702228 | 1/1997 | WIPO . |
| 9703943 | 2/1997 | WIPO . |
| 9708123 | 3/1997 | WIPO . |
| 9708127 | 3/1997 | WIPO . |

OTHER PUBLICATIONS

Van Leeuwen, P.W.N.M. et al., "The Hydroformylation of Butadiene Catalysed by Rhodium–Diphosphine Complexes." Journal of Molecular Catalysis (31), 1985, pp. 345–353.

Botteghi, Carlo et al., "Optically Active Aldehydes via Hydroformylation of 1,3–Dienes With Chiral Diphosphinerbodium Complexes." Journal of Organometallic Chemistry (184), 1980, pp. C17–C19.

Bertozzi, Sergio et al., "Selective Hydroformylation of Open–chain Conjugated Dienes Promoted by Mesitylene–solvated Rhodium Atoms to give B,y unsaturated Monoaldehydes." Journal of Organometallic Chemistry (487), 1995, pp. 41–45.

Fell, Bernhard et al., "The Hydroformylation of Conjugated Dienes V* Aliphatic Tertiary Phosphines and P–Substituted Phospholanes as Cocatalysis of the Rhodium–Catalysed Hydroformylation of 1,3–Dienes." Journal of Molecular Catalysis (2), 1977, pp. 211–218.

Bahrmann, H. et al., "The Hydroformylation of Conjugated Dienes Vi* Tertiary Aryl–and Arylalkyl–Phosphines as Ligands in the Rhodium Catalyed Hydroformylation Reaction of Conjugated Dienes to Dialdehydes." Journal of Molecular Catalysis (8), 1980, pp. 329–337.

Fell, Bernhard et al., "Reaction Products of a Hydroformylation of Conjugated Dienes with Rodium Carbonyl/tert–Phosphine Catalyst Systems." Chemical–Zeitung (99), 1975, pp.1–19.

*Primary Examiner*—Gary Geist
*Assistant Examiner*—Sreeni Padmanabhan
*Attorney, Agent, or Firm*—Gerald L. Coon

[57] ABSTRACT

This invention relates in part to processes for producing one or more substituted or unsubstituted aldehyde acid salts, e.g., epsilon caprolactam, which comprises subjecting said one or more substituted or unsubstituted unsaturated acid salts, e.g., pentenoic acid salts, to hydroformylation in the presence of a hydroformylation catalyst, e.g., a metal-organophosphorus ligand complex catalyst, to produce one or more substituted or unsubstituted aldehyde acid salts and/or one or more substituted or unsubstituted epsilon caprolactam precursors. This invention also relates in part to reaction mixtures containing one or more substituted or unsubstituted aldehyde acid salts as the principal product(s) of reaction.

15 Claims, No Drawings

PROCESS FOR PRODUCING ALDEHYDE ACID SALTS

BRIEF SUMMARY OF THE INVENTION

TECHNICAL FIELD

This invention relates in part to processes for producing one or more substituted or unsubstituted aldehyde acid salts. This invention also relates in part to reaction mixtures containing one or more substituted or unsubstituted aldehyde acid salts as the principal product(s) of reaction.

BACKGROUND OF THE INVENTION

Formylvaleric acid and formylvalerate esters are valuable intermediates which are useful, for example, in the production of epsilon caprolactam. The processes currently used to produce formylvaleric acid and/or formylvalerate esters have various disadvantages. For example, the prior art processes to formylvaleric acid and/or formylvalerate esters exhibit catalyst stability problems. Also, formylvaleric acid and/or formylvalerate ester selectivities may not be as high as desired. Accordingly, it would be desirable to produce epsilon caprolactam precursors by a process which does not have the disadvantages of prior art processes.

DISCLOSURE OF THE INVENTION

It has been discovered that unsaturated acid salts, e.g., pentenoic acid salts, can be hydroformylated to aldehyde acid salts, e.g., 5-formylvaleric acid salts, in high selectivities, i.e., higher selectivities than obtained hydroformylating pentenoic acids to formylvaleric acids or pentenoate esters to formylvalerate esters. In particular, it has been surprisingly discovered that such unsaturated acid salts possessing internal olefinic unsaturation can be hydroformylated to aldehyde acid salt products in high normal:branched isomer ratios, e.g., 3-pentenoic acid salts hydroformylated to 5-formylvaleric acid salts in high normal:branched isomer ratios. In addition, through the use of the salt compounds in accordance with this invention, the acid catalyzed degradation of organophosphite ligands and/or deactivation of metal-organophosphite ligand complex catalysts can be prevented or minimized. In addition, the use of bases to prepare salts of unsaturated acids and/or aldehyde acids may facilitate recovery of products by, for example, phase separation or solvent extraction.

This invention relates to a process for producing one or more substituted or unsubstituted aldehyde acid salts, e.g., formylvaleric acid salts such as triethylammonium 5-formylvalerate and ammonium 5-formylvalerate, and/or one or more substituted or unsubstituted epsilon caprolactam precursors which comprises subjecting one or more substituted or unsubstituted unsaturated acid salts, e.g., pentenoic acid salts such as triethylammonium 3-pentenoate and ammonium 3-pentenoate, to hydroformylation in the presence of a hydroformylation catalyst, e.g., a metal-organophosphorus ligand complex catalyst, to produce said one or more substituted or unsubstituted aldehyde acid salts and/or one or more substituted or unsubstituted epsilon caprolactam precursors.

This invention also relates in part to a process for producing a batchwise or continuously generated reaction mixture comprising:

(1) one or more substituted or unsubstituted 5-formylvaleric acid salts, e.g., triethylammonium 5-formylvalerate and ammonium 5-formylvalerate, and/or one or more substituted or unsubstituted epsilon caprolactam precursors;

(2) optionally one or more substituted or unsubstituted 4-formylvaleric acid salts and/or 3-formylvaleric acid salts;

(3) optionally one or more substituted or unsubstituted valeric acid salts; and (4) one or more substituted or unsubstituted pentenoic acid salts, e.g., triethylammonium 3-pentenoate and ammonium 3-pentenoate;

wherein the weight ratio of component (1) to the sum of components (2) and (3) is greater than about 0.1, preferably greater than about 0.25, more preferably greater than about 1.0; and the weight ratio of component (4) to the sum of components (1), (2) and (3) is about 0 to about 100, preferably about 0.001 to about 50;

which process comprises subjecting one or more substituted or unsubstituted pentenoic acid salts, e.g., triethylammonium 3-pentenoate and ammonium 3-pentenoate, to hydroformylation in the presence of a hydroformylation catalyst, e.g., a metal-organophosphorus ligand complex catalyst, to produce said batchwise or continuously generated reaction mixture.

This invention further relates to a process for producing a reaction mixture comprising one or more substituted or unsubstituted aldehyde acid salts, e.g., formylvaleric acid salts such as triethylammonium 5-formylvalerate and ammonium 5-formylvalerate, and/or one or more substituted or unsubstituted epsilon caprolactam precursors which process comprises subjecting one or more substituted or unsubstituted unsaturated acid salts, e.g., pentenoic acid salts such as triethylammonium 3-pentenoate and ammonium 3-pentenoate, to hydroformylation in the presence of a hydroformylation catalyst, e.g., a metal-organophosphorus ligand complex catalyst, to produce said reaction mixture comprising one or more substituted or unsubstituted aldehyde acid salts and/or one or more substituted or unsubstituted epsilon caprolactam precursors.

The processes of this invention can achieve high selectivities of pentenoic acid salts to formylvaleric acid salts. Selectivities of formylvaleric acid salts of at least 10% by weight and up to 75% by weight or greater may be achieved by the processes of this invention. Also, the processes of this invention can achieve high normal:branched isomer ratios, e.g., pentenoic acid salts hydroformylated to 5-formylvaleric acid salts in high normal:branched isomer ratios.

This invention yet further relates in part to a batchwise or continuously generated reaction mixture comprising:

(1) one or more substituted or unsubstituted 5-formylvaleric acid salts, e.g., triethylammonium 5-formylvalerate and ammonium 5-formylvalerate, and/or one or more substituted or unsubstituted epsilon caprolactam precursors;

(2) optionally one or more substituted or unsubstituted 4-formylvaleric acid salts and/or 3-formylvaleric acid salts;

(3) optionally one or more substituted or unsubstituted valeric acid salts; and (4) one or more substituted or unsubstituted pentenoic acid salts, e.g., triethylammonium 3-pentenoate and ammonium 3-pentenoate;

wherein the weight ratio of component (1) to the sum of components (2) and (3) is greater than about 0.1, preferably greater than about 0.25, more preferably greater than about 1.0; and the weight ratio of component (4) to the sum of components (1), (2) and (3) is about 0 to about 100, preferably about 0.001 to about 50.

This invention also relates in part to a reaction mixture comprising one or more substituted or unsubstituted aldehyde acid salts, e.g., formylvaleric acid salts such as triethylammonium 5-formylvalerate and ammonium 5-formylvalerate, and/or one or more substituted or unsubstituted epsilon caprolactam precursors in which said reaction mixture is prepared by a process which comprises subjecting one or more substituted or unsubstituted unsaturated acid salts, e.g., pentenoic acid salts such as triethylammonium 3-pentenoate and ammonium 3-pentenoate, to hydroformylation in the presence of a hydroformylation catalyst, e.g., a metal-organophosphorus ligand complex catalyst, to produce said reaction mixture comprising one or more substituted or unsubstituted aldehyde acid salts and/or one or more substituted or unsubstituted epsilon caprolactam precursors.

The reaction mixtures of this invention are distinctive insofar as the processes for their preparation achieve the generation of high selectivities of aldehyde acid salts in a manner which can be suitably employed in a commercial process for the manufacture of aldehyde acid salts. In particular, the reaction mixtures of this invention are distinctive insofar as the processes for their preparation allow for the production of aldehyde acid salts in relatively high yields without generating large amounts of byproducts, e.g., valeric acid salts.

DETAILED DESCRIPTION

The hydroformylation processes of this invention involve the production of aldehyde acid salts, e.g., formylvaleric acid salts, and/or one or more substituted or unsubstituted epsilon caprolactam precursors by reacting an unsaturated acid salt, e.g., pentenoic acid salt, with carbon monoxide and hydrogen in the presence of a solubilized metal-ligand complex catalyst and free ligand in a liquid medium that also contains a solvent for the catalyst and ligand. The processes may be carried out in a continuous single pass mode in a continuous gas recycle manner or more preferably in a continuous liquid catalyst recycle manner as described below. The hydroformylation processing techniques employable herein may correspond to any known processing techniques such as preferably employed in conventional liquid catalyst recycle hydroformylation reactions. As used herein, the term "hydroformylation" is contemplated to include, but is not limited to, all permissible hydroformylation processes which involve converting one or more substituted or unsubstituted unsaturated acid salts to one or more substituted or unsubstituted aldehyde acid salts and/or one or more substituted or unsubstituted epsilon caprolactam precursors. In general, the hydroformylation step or stage comprises reacting one or more substituted or unsubstituted unsaturated acid salts with carbon monoxide and hydrogen in the presence of a catalyst to produce one or more substituted or unsubstituted aldehyde acid salts. As used herein, substituted or unsubstituted epsilon caprolactam precursors is contemplated to include, but are not limited to, one or more formylvaleric acid salts, iminocaproic acid and/or salts thereof, aminocaproic acid and/or salts thereof, caprolactam, caprolactone, imines, hemiaminals, imides, amides or amines derived from formylvaleric acid and its salts, and the corresponding dimers, trimers and oligomers.

The hydroformylation reaction mixtures employable herein includes any solution derived from any corresponding hydroformylation process that may contain at least some amount of four different main ingredients or components, i.e., the aldehyde acid salt product and/or epsilon caprolactam precursors, a metal-ligand complex catalyst, optionally free ligand and an organic solubilizing agent for said catalyst and said free ligand, said ingredients corresponding to those employed and/or produced by the hydroformylation process from whence the hydroformylation reaction mixture starting material may be derived. By "free ligand" is meant ligand that is not complexed with (tied to or bound to) the metal, e.g., rhodium atom, of the complex catalyst. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted unsaturated acid salt starting material, carbon monoxide and hydrogen gases, and in situ formed type products, such as saturated hydrocarbons and/or unreacted isomerized olefins corresponding to the unsaturated acid salt starting materials, and high boiling liquid condensation byproducts, as well as other inert co-solvent type materials or hydrocarbon additives, if employed.

The catalysts useful in the hydroformylation process of this invention include metal-ligand complex catalysts. The permissible metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. The permissible ligands include, for example, organophosphorus, organoarsenic and organoantimony ligands, or mixtures thereof, preferably organophosphorus ligands. The permissible organophosphorus ligands which make up the metal-ligand complexes include organophosphines, e.g., mono-, di-, tri- and poly-(organophosphines), and organophosphites, e.g., mono-, di-, tri- and poly-(organophosphites). Other permissible organophosphorus ligands include, for example, organophosphonites, organophosphinites, amino phosphines and the like. Still other permissible ligands include, for example, heteroatom-containing ligands such as described in U.S. patent application Ser. No. 08/818,781, filed Mar. 10, 1997, the disclosure of which is incorporated herein by reference. Mixtures of such ligands may be employed if desired in the metal-ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

The term "complex" as used herein and in the claims means a coordination compound formed by the union of one or more electronically rich molecules or atoms capable of independent existence with one or more electronically poor molecules or atoms, each of which is also capable of independent existence. For example, the ligands employable herein, i.e., organophosphorus ligands, may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, pentenoate, acetylacetonate, $SO_4$, $BF_4$, $PF_6$, $NO_2$, $NO_3$, $CH_3O$, $CH_2=CHCH_2$, $CH_2=CHCH_2CH_3$, $CH_3CH=CHCH_2$, $C_6H_5CN$, $CH_3CN$, NO, $NH_3$, pyridine, $(C_2H_5)_3N$, mono-olefins, diolefins and triolefins, tetrahydrofuran, and the like. It is of course to be understood that the complex species are preferably free of any additional organic ligand or anion that might poison the catalyst and have an undue adverse effect on catalyst performance. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one phosphorus-containing molecule complexed per metal, e.g., rhodium. As noted above, it is considered that the catalytic species of the preferred catalyst employed in the hydroformylation reaction may be complexed with carbon monoxide and hydrogen in addition to the organophosphorus ligands in view of the carbon monoxide and hydrogen gas employed by the hydroformylation reaction.

Among the organophosphines that may serve as the ligand of the metal-organophosphine complex catalyst and/or free organophosphine ligand of the hydroformylation reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl diphosphines and bisphosphine mono oxides, as well as ionic triorganophosphines containing at least one ionic moiety selected from the salts of sulfonic acid, of carboxylic acid, of phosphonic acid and of quaternary ammonium compounds, and the like. Of course any of the hydrocarbon radicals of such tertiary non-ionic and ionic organophosphines may be substituted if desired, with any suitable substituent that does not unduly adversely affect the desired result of the hydroformylation reaction. The organophosphine ligands employable in the hydroformylation reaction and/or methods for their preparation are known in the art.

Illustrative triorganophosphine ligands may be represented by the formula:

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radicals include, e.g., alkyl radicals, alkoxy radicals, silyl radicals such as —$Si(R^2)_3$; amino radicals such as —$N(R^2)_2$; acyl radicals such as —$C(O)R^2$; carboxy radicals such as —$C(O)OR^2$; acyloxy radicals such as —$OC(O)R^2$; amido radicals such as —$C(O)N(R^2)_2$ and —$N(R^2)C(O)R^2$; ionic radicals such as —$SO_3M$ wherein M represents inorganic or organic cationic atoms or radicals; sulfonyl radicals such as —$SO_2R^2$; ether radicals such as —$OR^2$; sulfinyl radicals such as —$SOR^2$; sulfenyl radicals such as —$SR^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —$N(R^2)_2$, each $R^2$ taken together can also represent a divalent bridging group that forms a heterocyclic radical with the nitrogen atom and in amido substituents such as $C(O)N(R^2)_2$ and —$N(R^2)C(O)R^2$ each —$R^2$ bonded to N can also be hydrogen. Illustrative alkyl radicals include, e.g., methyl, ethyl, propyl, butyl and the like. Illustrative aryl radicals include, e.g., phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific organophosphines include, e.g., triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, DIOP, i.e., (4R,5R)-(-)-O-isopropylidene-2,3-dihydroxy-1,4-bis(diphenylphosphino) butane and/or (4S,5S)-(+)-O-isopropylidene-2,3-dihydroxy-1,4-bis(diphenylphosphino)butane and/or (4S,5R)-(-)-O-isopropylidene-2,3-dihydroxy-1,4-bis(diphenylphosphino) butane, substituted or unsubstituted bicyclic bisphosphines such as 1,2-bis(1,4-cyclooctylenephosphino)ethane, 1,3-bis (1,4-cyclooctylenephosphino)propane, 1,3-bis(1,5-cyclooctylenephosphino)propane and 1,2-bis(2,6-dimethyl-1,4-cyclooctylenephosphino)ethane, substituted or unsubstituted bis(2,2'-diphenylphosphinomethyl)biphenyl such as bis(2,2'-diphenylphosphinomethyl)biphenyl and bis{2,2'-di(4-fluorophenyl)phosphinomethyl}biphenyl, xantphos, thixantphos, bis(diphenylphosphino)ferrocene, bis(diisopropylphosphino)ferrocene, bis (diphenylphosphino)ruthenocene, as well as the alkali and alkaline earth metal salts of sulfonated triphenylphosphines, e.g., of (tri-m-sulfophenyl)phosphine and of (m-sulfophenyl)diphenyl-phosphine and the like.

More particularly, illustrative metal-organophosphine complex catalysts and illustrative free organophosphine ligands include, e.g., those disclosed in U.S. Pat. Nos. 3,527,809; 4,148,830; 4,247,486; 4,283,562; 4,400,548; 4,482,749, 4,861,918; 4,694,109; 4,742,178; 4,851,581; 4,824,977; 5,332,846; 4,774,362; and WO Patent Application No. 95/30680, published Nov. 16, 1995; the disclosures of which are incorporated herein by reference.

The organophosphites that may serve as the ligand of the metal-organophosphite ligand complex catalyst and/or free ligand of the processes and reaction product mixtures of this invention may be of the achiral (optically inactive) or chiral (optically active) type and are well known in the art.

Among the organophosphites that may serve as the ligand of the metal-organophosphite complex catalyst and/or free organophosphite ligand of the hydroformylation reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

 (II)

wherein $R^3$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, e.g., in U.S. Pat. No. 4,567,306, the disclosure of which is incorporated herein by reference.

Representative diorganophosphites may include those having the formula:

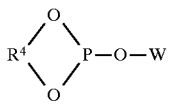 (III)

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by $R^4$ include divalent acyclic radicals and divalent aromatic radicals. Illustrative divalent acyclic radicals include, e.g., alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, e.g., in U.S. Pat. Nos. 3,415,906 and 4,567,302 and the like, the disclosures of which are incorporated herein by reference. Illustrative divalent aromatic radicals include, e.g., arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably $R^4$ is a divalent aromatic radical such as disclosed more fully, e.g., in U.S. Pat. Nos. 4,599,206 and 4,717,775, and the like, the disclosures of which are incorporated herein by reference.

Representative of a more preferred class of diorganophosphites are those of the formula:

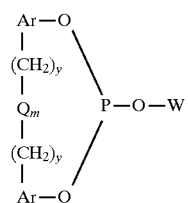 (IV)

wherein W is as defined above, each Ar is the same or different and represents a substituted or unsubstituted aryl radical, each y is the same or different and is a value of 0 or 1, Q represents a divalent bridging group selected from $-C(R^5)_2-$, $-O-$, $-S-$, $-NR^6-$, $Si(R^7)_2-$ and $-CO-$, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1. Such diorganophosphites are described in greater detail, e.g., in U.S. Pat. Nos. 4,599,206 and 4,717,775, the disclosures of which are incorporated herein by reference.

Representative triorganophosphites may include those having the formula:

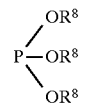 (V)

wherein each $R^8$ is the same or different and is a substituted or unsubstituted monovalent hydrocarbon radical, e.g., an alkyl or aryl radical. Suitable hydrocarbon radicals may contain from 1 to 24 carbon atoms or greater and may include those described above for $R^1$ in formula (I).

Representative organopolyphosphites contain two or more tertiary (trivalent) phosphorus atoms and may include those having the formula:

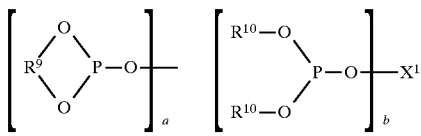 (VI)

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^9$ radical may be the same or different, and when b has a value of 1 or more, each $R^{10}$ radical may also be the same or different.

Representative n-valent (preferably divalent) hydrocarbon bridging radicals represented by $X^1$, as well as representative divalent hydrocarbon radicals represented by $R^9$ above, include both acyclic radicals and aromatic radicals, such as alkylene, alkylene-$Q_m$-alkylene, cycloalkylene, arylene, bisarylene, arylene-alkylene, and arylene-$(CH_2)_y-$$Q_m-(CH_2)_y$-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, e.g., in U.S. Pat. Nos. 3,415,906; 4,567,306; 4,599,206; 4,769,498; 4,717,775; 4,885,401; 5,202,297; 5,264,616 and 5,364,950, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

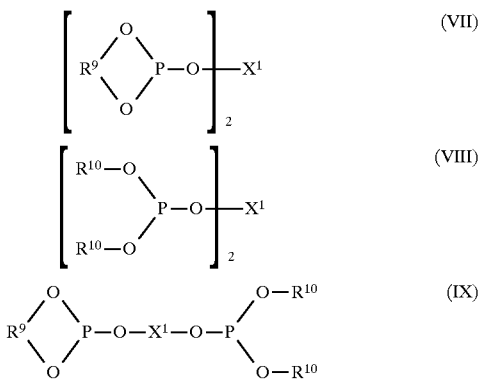

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Phosphite ligands of such formulas (VI) to (IX) may be found disclosed, e.g., in said U.S. Pat. Nos. 4,668,651; 4,748,261; 4,769,498; 4,885,401; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following formulas (X) to (XII):

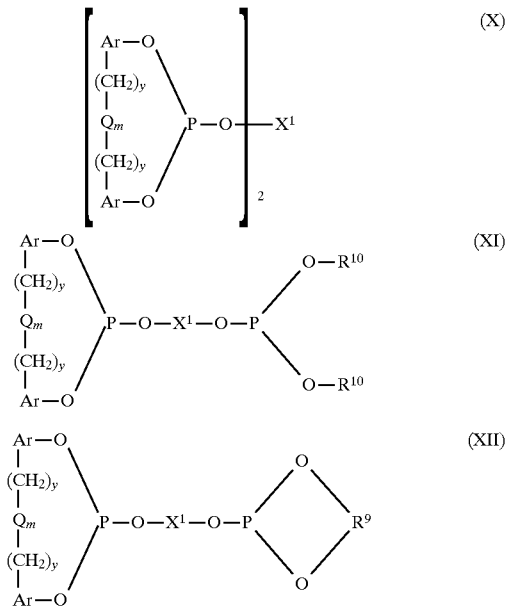

wherein Ar, Q, $R^9$, $R^{10}$, $X^1$, m and y are as defined above. Most preferably $X^1$ represents a divalent aryl-$(CH_2)_y$—$(Q)_m$—$(CH_2)_y$-aryl radical wherein each y individually has a value of 0 or 1; m has a value of 0 or 1 and Q is —O—, —S— or —$C(R^5)_2$— wherein each $R^5$ is the same or different and represents a hydrogen or methyl radical. More preferably each alkyl radical of the above defined RIO groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulas. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organophosphite in the above formulas (VI) to (XII) may be an ionic phosphite, i.e., may contain one or more ionic moieties selected from the group consisting of:

$SO_3M$ wherein M represents an inorganic or organic cation, $PO_3M$ wherein M represents an inorganic or organic cation, $N(R^{11})_3X^2$ wherein each $R^{11}$ is the same or different and represents a hydrocarbon radical containing from 1 to 30 carbon atoms, e.g, alkyl, aryl, alkaryl, aralkyl, and cycloalkyl radicals, and $X^2$ represents an inorganic or organic anion, $CO_2M$ wherein M represents an inorganic or organic cation, as described, e.g., in U.S. Pat. Nos. 5,059,710; 5,113,022, 5,114,473 and 5,449,653, the disclosures of which are incorporated herein by reference. Thus, if desired, such phosphite ligands may contain from 1 to 3 such ionic moieties, while it is preferred that only one such ionic moiety be substituted on any given aryl moiety in the phosphite ligand when the ligand contains more than one such ionic moiety. As suitable counter-ions, M and $X^2$, for the anionic moieties of the ionic phosphites there can be mentioned hydrogen (i.e. a proton), the cations of the alkali and alkaline earth metals, e.g., lithium, sodium, potassium, cesium, rubidium, calcium, barium, magnesium and strontium, the ammonium cation, quaternary ammonium cations, phosphonium cations, arsonium cations and iminium cations. Suitable anionic atoms or radicals include, for example, sulfate, carbonate, phosphate, chloride, acetate, oxalate and the like.

Of course any of the $R^9$, $R^{10}$, $X^2$ and Ar radicals of such non-ionic and ionic organophosphites of formulas (VI) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as -$Si(R^{12})_3$; amino radicals such as —$N(R^{12})_2$; phosphine radicals such as -aryl-$P(R^{12})_2$; acyl radicals such as —$C(O)R^{12}$; acyloxy radicals such as —$OC(O)R^{12}$; amido radicals such as —$CON(R^{12})_2$ and —$N(R^{12})COR^{12}$; sulfonyl radicals such as —$SO_2R^{12}$; alkoxy radicals such as —$OR^{12}$; sulfinyl radicals such as —$SOR^{12}$; sulfenyl radicals such as —$SR^{12}$; phosphonyl radicals such as —$P(O)(R^{12})_2$; as well as, halogen, nitro, cyano, trifluoromethyl, hydroxy radicals, and the like, wherein each $R^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —N(R$^{12}$)$_2$ each $R^{12}$ taken together can also represent a divalent bridging group that forms a heterocyclic radical with the nitrogen atom, and in amido substituents such as —C(O)N(R$^{12}$)$_2$ and —N(R$^{12}$)COR$^{12}$ each $R^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —(OCH$_2$CH$_2$)$_2$OCH$_3$, —(OCH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$),and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfenyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, P(O)CH$_3$(C$_6$H$_5$), —P(O)(H)(C$_6$H$_5$), and the like.

Specific illustrative examples of such organophosphite ligands include the following:

2-t-butyl-4-methoxyphenyl(3,3'-di-t-butyl-,5,5'-dimethoxy-1,1'-biphenyl-2,2'-diyl)phosphite having the formula:

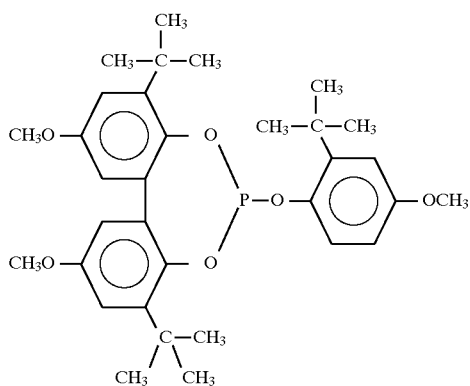

Ligand A methyl(3,3'-di-t-butyl-5,5'-dimethoxy-1,1'-biphenyl-2,2'-diyl)phosphite having the formula:

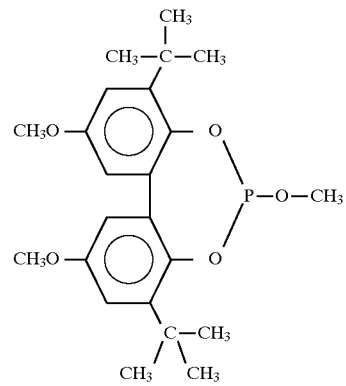

Ligand B 6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

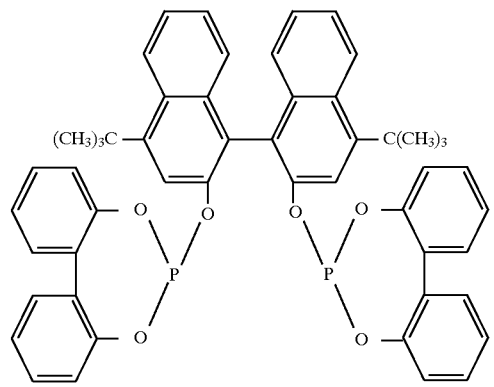

Ligand C 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin having the formula:

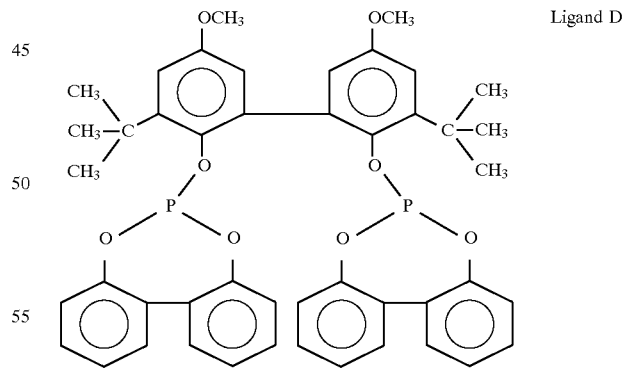

Ligand D 6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

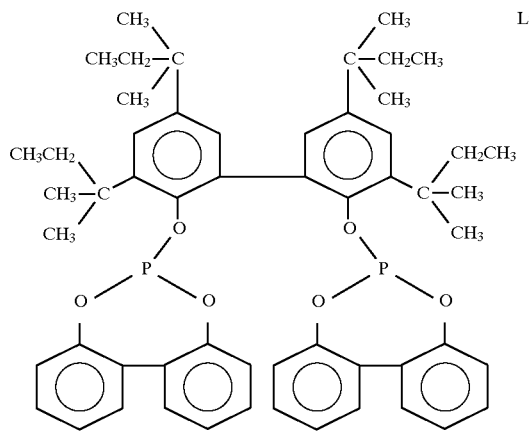
6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin having the formula:
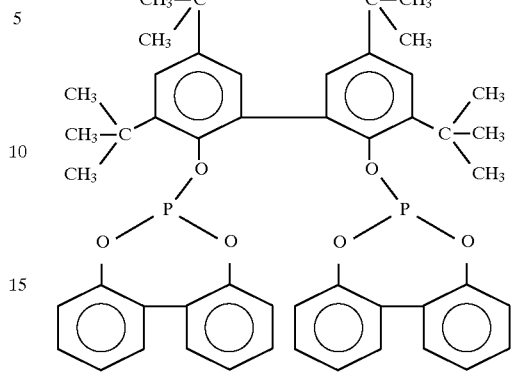
(2R,4R)-di[2,2'-(3,3',5,5'-tetrakis-tert-amyl-1,1'-biphenyl)]-2,4-pentyldiphosphite having the formula:
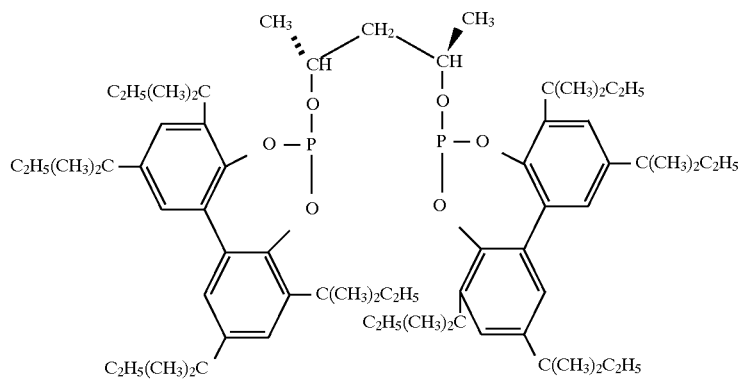
(2R,4R)-di [2,2'-(3,3',5,5'-tetrakis-tert-butyl-1,1'-biphenyl)]-2,4-pentyldiphosphite having the formula:
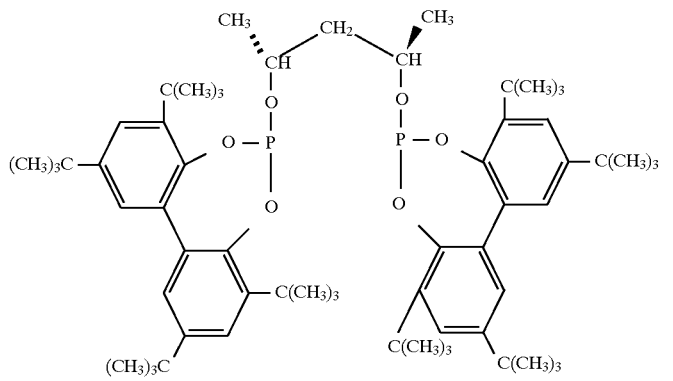
(2R,4R)-di [2,2'-(3,3'-di-amyl-5,5'-dimethoxy-1,1'-biphenyl)]-2,4-pentyldiphosphite having the formula:

Ligand I
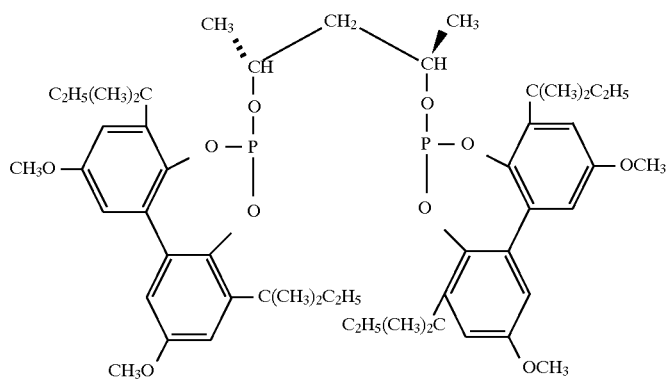
(2R,4R)-di [2,2'-(3,3'-di-tert-butyl-5,5'-dimethyl-1,1'-biphenyl)]-2,4-pentyldiphosphite having the formula:
(2R,4R)-di[2,2'-(3,3'-di-tert-butyl-5,5'-diethoxy-1,1'-biphenyl)]-2,4-pentyldiphosphite having the formula:
Ligand J
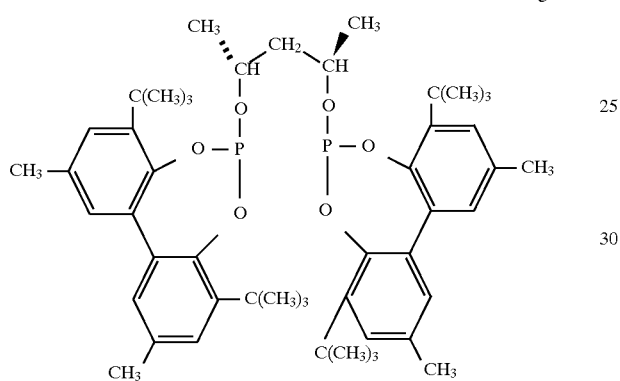
Ligand K
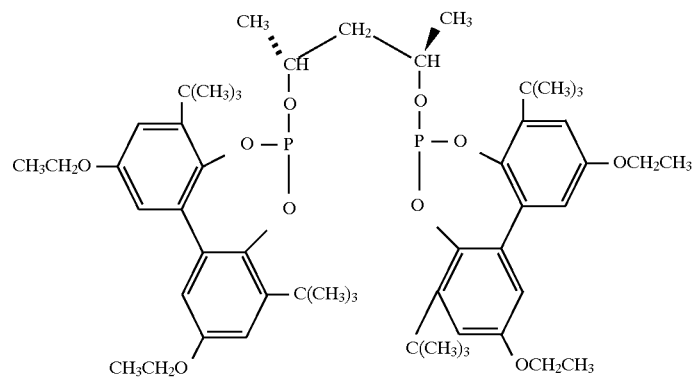
(2R,4R)-di[2,2'-(3,3'-di-tert-butyl-5,5'-diethyl-1,1'-biphenyl)]-2,4-pentyldiphosphite having the formula:

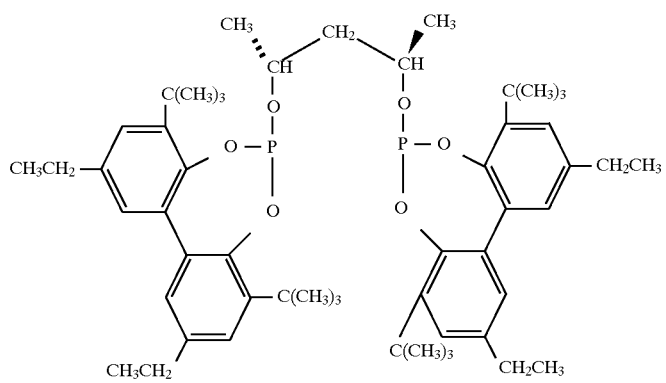

Ligand L (2R,4R)-di[2,2'-(3,3'-di-tert-butyl-5,5'-dimethoxy-1,1'-biphenyl)]-2,4-pentyldiphosphite having the formula:

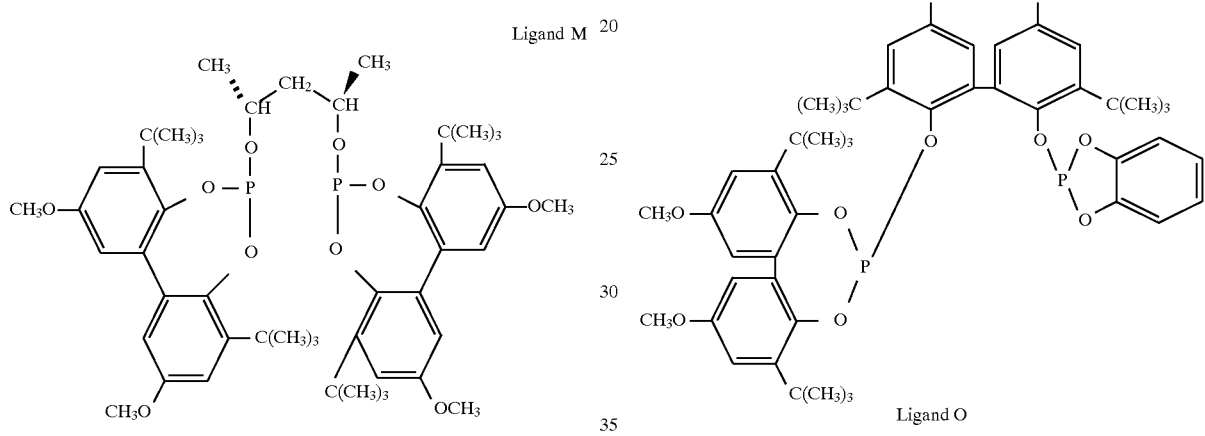

Ligand M

Ligand O

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

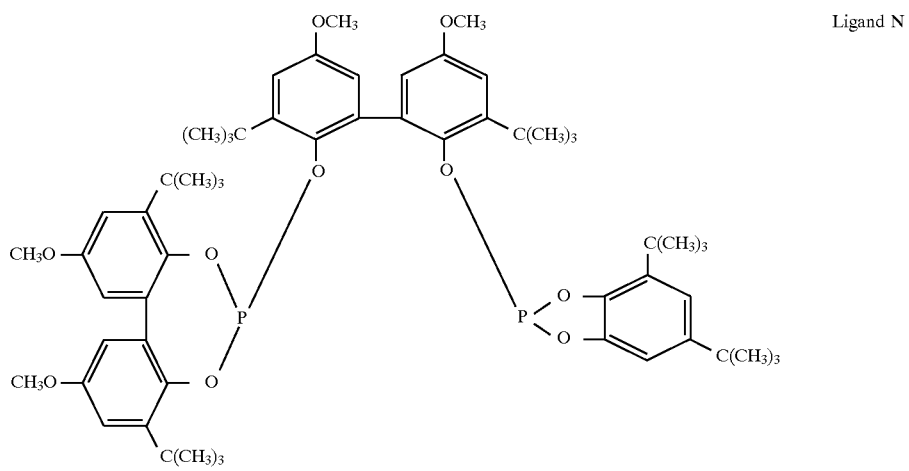

Ligand N

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

19

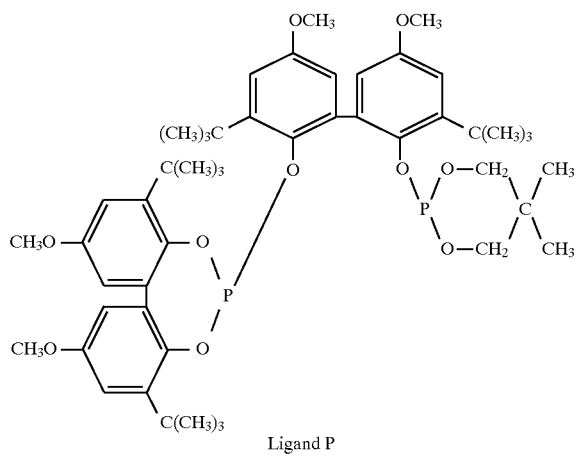

Ligand P

2'-[[4,8-bis(1,1-dimethylethyl)-2,10-dimethoxydibenzo [d,f][1,3,2]-dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

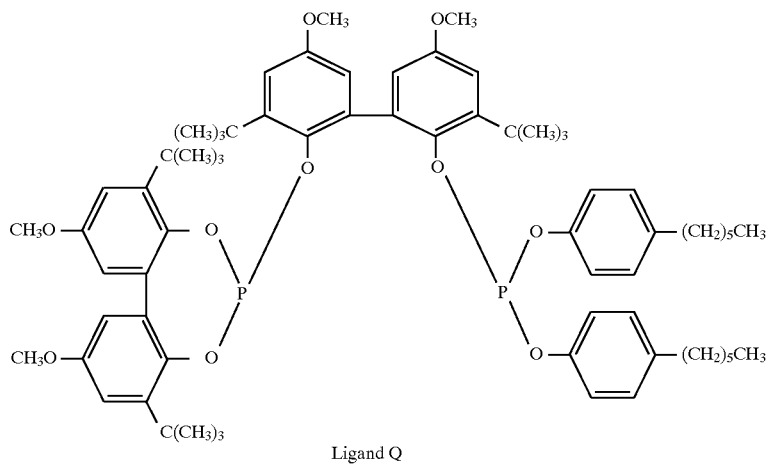

Ligand Q

2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, 6-(1,1-dimethylethyl)phenyl diphenyl ester of phosphorous acid having the formula:

20

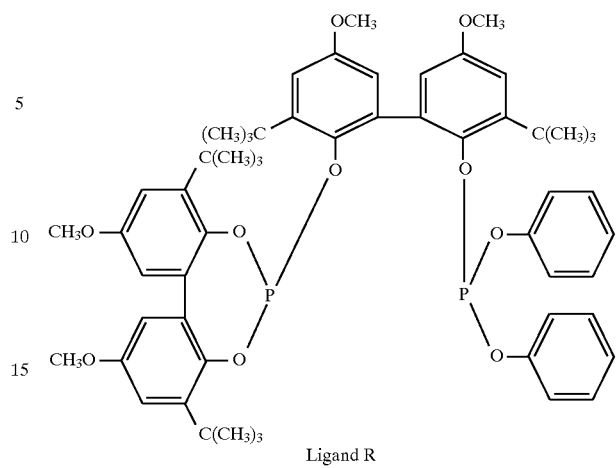

Ligand R 3-methoxy-1,3-cyclohexamethylene tetrakis[3,6-bis(1,1-dimethylethyl)-2-naphthalenyl]ester of phosphorous acid having the formula:

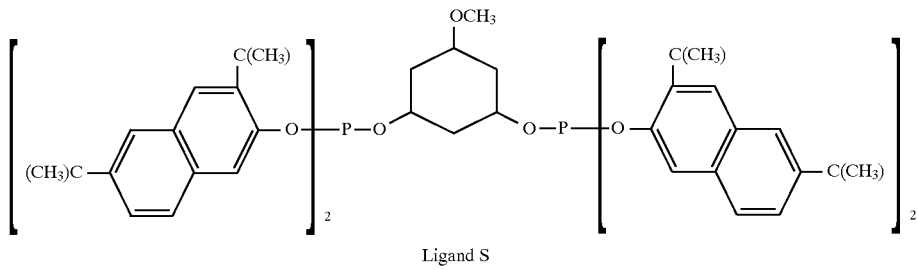

Ligand S 2,5-bis(1,1-dimethylethyl)-1,4-phenylene tetrakis[2,4-bis(1,1-dimethylethyl)phenyl]ester of phosphorous acid having the formula:

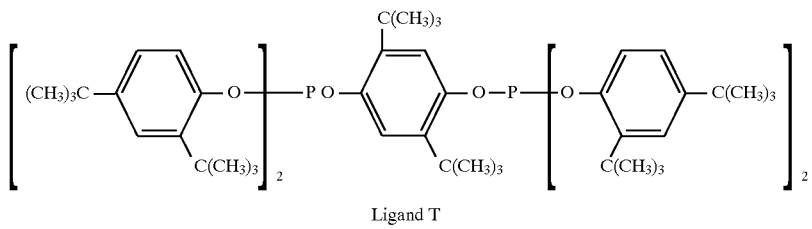

Ligand T methylenedi-2,1-phenylene tetrakis[2,4-bis(1,1-dimethylethyl)phenyl]ester of phosphorous acid having the formula:

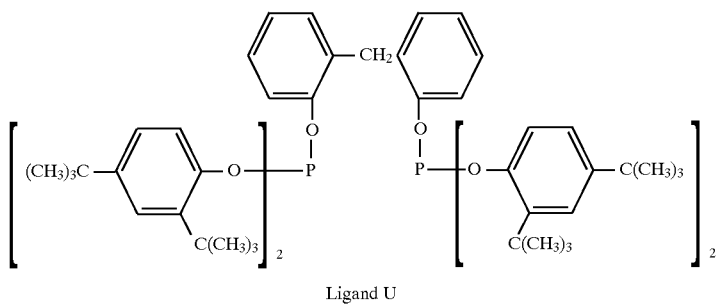

Ligand U

[1,1'-biphenyl]-2,2'-diyl tetrakis[2-(1,1-dimethylethyl)-4-methoxyphenyl]ester of phosphorous acid having the formula:

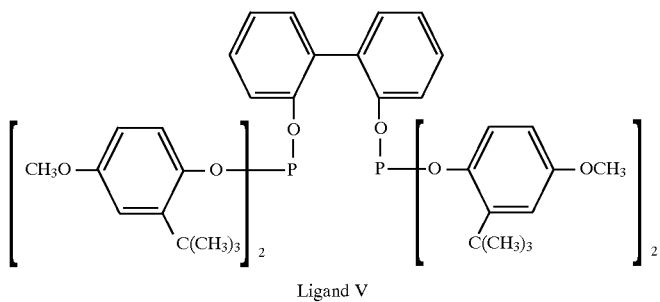

Ligand V

Still other illustrative organophosphorus ligands useful in this invention include those disclosed in U.S. patent application Ser. No. (08/843,389), filed on an even date herewith, the disclosure of which is incorporated herein by reference.

The metal-ligand complex catalysts employable in this invention may be formed by methods known in the art. The metal-ligand complex catalysts may be in homogeneous or heterogeneous form. For instance, preformed metal hydrido-carbonyl-organophosphorus ligand catalysts may be prepared and introduced into the reaction mixture of a hydroformylation process. More preferably, the metal-ligand complex catalysts can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment of this invention, rhodium dicarbonyl acetylacetonate is employed as a rhodium precursor and reacted in the presence of a solvent with the organophosphorus ligand to form a catalytic rhodium-organophosphorus ligand complex precursor which is introduced into the reactor along with excess free organophosphorus ligand for the in situ formation of the active catalyst. In any event, it is sufficient for the purpose of this invention that carbon monoxide, hydrogen and organophosphorus compound are all ligands that are capable of being complexed with the metal and that an active metal-ligand catalyst is present in the reaction mixture under the conditions used in the hydroformylation reaction.

More particularly, a catalyst precursor composition can be formed consisting essentially of a solubilized metal-ligand complex precursor catalyst, an organic solvent and free ligand. Such precursor compositions may be prepared by forming a solution of a metal starting material, such as a metal oxide, hydride, carbonyl or salt, e.g. a nitrate, which may or may not be in complex combination with a ligand as defined herein. Any suitable metal starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organophosphorus ligand rhodium carbonyl hydrides. Carbonyl and organophosphorus ligands, if not already complexed with the initial metal, may be complexed to the metal either prior to or in situ during the hydroformylation process.

By way of illustration, the preferred catalyst precursor composition of this invention consists essentially of a solubilized rhodium carbonyl organophosphorus ligand complex precursor catalyst, a solvent and free organophosphorus ligand prepared by forming a solution of rhodium dicarbonyl acetylacetonate, an organic solvent and a ligand as defined herein. The organophosphorus ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphorus ligand complex precursor are soluble can be employed. The amounts of rhodium complex catalyst precursor, organic solvent and organophosphorus ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphorus ligand, to form the active complex catalyst as explained above. In a continuous process, the acetylacetone which is freed from the precursor catalyst under hydroformylation conditions is removed from the reaction medium with the product aldehyde salt and thus is in no way detrimental to the hydroformylation process. The use of such preferred rhodium complex catalytic precursor compositions provides a simple economical and efficient method for handling the rhodium precursor metal and hydroformylation start-up.

Accordingly, the metal-ligand complex catalysts used in the process of this invention consists essentially of the metal complexed with carbon monoxide and a ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants. The hydrogen and/or carbonyl ligands of an active metal-ligand complex catalyst may be present as a result of being ligands bound to a precursor catalyst and/or as a result of in situ formation, e.g., due to the hydrogen and carbon monoxide gases employed in hydroformylation process of this invention.

As noted the hydroformylation reactions involve the use of a metal-ligand complex catalyst as described herein. Of course mixtures of such catalysts can also be employed if desired. The amount of metal-ligand complex catalyst present in the reaction medium of a given hydroformylation reaction need only be that minimum amount necessary to provide the given metal concentration desired to be employed and which will furnish the basis for at least the catalytic amount of metal necessary to catalyze the particular hydroformylation reaction involved such as disclosed e.g. in the above-mentioned patents. In general, the catalyst concentration can range from several parts per million to several percent by weight. Organophosphorus ligands can be employed in the above-mentioned catalysts in a molar ratio of generally from about 0.5:1 or less to about 1000:1 or greater. The catalyst concentration will be dependent on the hydroformylation reaction conditions and solvent employed.

In general, the organophosphorus ligand concentration in hydroformylation reaction mixtures may range from between about 0.005 and 25 weight percent based on the total weight of the reaction mixture. Preferably the ligand concentration is between 0.01 and 15 weight percent, and more preferably is between about 0.05 and 10 weight percent on that basis.

In general, the concentration of the metal in the hydroformylation reaction mixtures may be as high as about 2000 parts per million by weight or greater based on the weight of the reaction mixture. Preferably the metal concentration is between about 50 and 1000 parts per million by weight based on the weight of the reaction mixture, and more preferably is between about 70 and 800 parts per million by weight based on the weight of the reaction mixture.

In addition to the metal-ligand complex catalyst, free ligand (i.e., ligand that is not complexed with the metal) may also be present in the hydroformylation reaction medium. The free ligand may correspond to any of the above-defined ligands discussed above as employable herein. It is preferred that the free ligand be the same as the ligand of the metal-ligand complex catalyst employed. However, such ligands need not be the same in any given process. The hydroformylation reaction may involve up to 100 moles, or higher, of free ligand per mole of metal in the hydroformylation reaction medium. Preferably the hydroformylation reaction is carried out in the presence of from about 0.25 to about 50 moles of coordinatable phosphorus, and more preferably from about 0.5 to about 30 moles of coordinatable phosphorus per mole of metal present in the reaction medium; said amounts of coordinatable phosphorus being the sum of both the amount of coordinatable phosphorus that is bound (complexed) to the metal present and the amount of free (non-complexed) coordinatable phosphorus present. Of course, if desired, make-up or additional coordinatable phosphorus can be supplied to the reaction medium of the hydroformylation reaction at any time and in any suitable manner, e.g. to maintain a predetermined level of free ligand in the reaction medium.

As indicated above, the hydroformylation catalyst may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

As an illustration, the rhodium catalyst may be impregnated onto any solid support, such as inorganic oxides, (e.g., alumina, silica, titania, or zirconia) carbon, or ion exchange resins. The catalyst may be supported on, or intercalated inside the pores of, a zeolite or glass; the catalyst may also be dissolved in a liquid film coating the pores of said zeolite or glass. Such zeolite-supported catalysts are particularly advantageous for producing one or more regioisomeric aldehydes in high selectivity, as determined by the pore size of the zeolite. The techniques for supporting catalysts on solids, such as incipient wetness, which will be known to those skilled in the art. The solid catalyst thus formed may still be complexed with one or more of the ligands defined above. Descriptions of such solid catalysts may be found in for example: J. Mol. Cat. 1991, 70, 363–368; Catal. Lett. 1991, 8, 209–214; J. Organomet. Chem, 1991, 403, 221–227; Nature, 1989, 339, 454–455; J. Catal. 1985, 96, 563–573; J. Mol. Cat. 1987, 39, 243–259.

The rhodium catalyst may be attached to a thin film or membrane support, such as cellulose acetate or polyphenylenesulfone, as described in for example J. Mol. Cat. 1990, 63, 213–221.

The rhodium catalyst may be attached to an insoluble polymeric support through an organophosphorus-containing ligand, such as a phosphine or phosphite, incorporated into the polymer. Such polymer-supported ligands are well known, and include such commercially available species as the divinylbenzene/polystyrene-supported triphenylphosphine. The supported ligand is not limited by the choice of polymer or phosphorus-containing species incorporated into it. Descriptions of polymer-supported catalysts may be found in for example: J. Mol. Cat. 1993, 83, 17–35; Chemtech 1983, 46; J. Am. Chem. Soc. 1987, 109, 7122–7127.

In the heterogeneous catalysts described above, the catalyst may remain in its heterogeneous form during the entire hydroformylation and catalyst separation process. In another embodiment of the invention, the catalyst may be supported on a polymer which, by the nature of its molecular weight, is soluble in the reaction medium at elevated temperatures, but precipitates upon cooling, thus facilitating catalyst separation from the reaction mixture. Such "soluble" polymer-supported catalysts are described in for example: Polymer, 1992, 33, 161; J. Org. Chem. 1989, 54, 2726–2730.

When the rhodium catalyst is in a heterogeneous or supported form, the reaction is carried out in the slurry phase due to the high boiling points of the products, and to avoid decomposition of the product aldehyde salts. The catalyst may then be separated from the product mixture by filtration or decantation.

Illustrative substituted and unsubstituted unsaturated acid salts that can be used in the hydroformylation process of this invention include one or more of the following: alkenoic acid salts such as triethylammonium 3-pentenoate, ammonium 3-pentenoate, octyltriethylammonium 3-pentenoate, including mixtures comprising one or more unsaturated acid salts. Illustrative of suitable substituted and unsubstituted unsaturated acid salts include those permissible substituted and unsubstituted unsaturated acid salts which are described in Kirk-Othmer, Encyclopedia of Chemical Technology, Fourth Edition, 1996, the pertinent portions of which are incorporated herein by reference. The substituted and unsubstituted unsaturated acid salts can be prepared by conventional methods or by the procedures disclosed in copending U.S. patent application Ser. Nos. 08/839,576 and 08/843,340, both filed on an even date herewith, the disclosures of which are incorporated herein by reference. Reaction mixtures comprising unsaturated acid salts may be useful herein. The amount of unsaturated acid salts employed in the hydroformylation process of this invention is not narrowly critical and can be any amount sufficient to produce aldehyde acid salts, preferably in high selectivities.

The hydroformylation reaction conditions may include any suitable type hydroformylation conditions heretofore employed for producing aldehydes. For instance, the total gas pressure of hydrogen, carbon monoxide and other components of the hydroformylation process may range from about 1 to about 10,000 psia. In general, the hydroformylation process is operated at a total gas pressure of hydrogen, carbon monoxide and all other components of less than about 1500 psia and more preferably less than about 1000 psia, the minimum total pressure being limited predominately by the amount of reactants necessary to obtain a desired rate of reaction. The total pressure employed in the hydroformylation reaction may range in general from about 20 to about 3000 psia, preferably from about 50 to 2000 psia and more preferably from about 75 to about 1000 psia. The total pressure of the hydroformylation process will be dependent on the particular catalyst system employed.

More specifically, the carbon monoxide partial pressure of the hydroformylation reaction in general may range from about 1 to about 3000 psia, and preferably from about 3 to about 1500 psia, while the hydrogen partial pressure in general may range from about 1 to about 3000 psia, and preferably from about 3 to about 1500 psia. In general, the molar ratio of carbon monoxide to gaseous hydrogen may range from about 100:1 or greater to about 1:100 or less, the preferred carbon monoxide to gaseous hydrogen molar ratio being from about 1:10 to about 10:1. The carbon monoxide and hydrogen partial pressures will be dependent in part on the particular catalyst system employed.

Carbon monoxide partial pressure should be sufficient for the hydroformylation reaction, e.g., of a pentenoic acid salt to a formylvaleric acid salt, to occur at an acceptable rate, but not so extreme that reaction rate and/or normal/branched aldehyde ratio may become unacceptably low. Hydrogen partial pressure must be sufficient for the hydroformylation reaction to occur at an acceptable rate, but not so high that hydrogenation of starting materials and intermediates, or isomerization of intermediates to undesired isomers, occurs. It is understood that carbon monoxide and hydrogen can be employed separately, in mixture with each other, i.e., synthesis gas, or may be produced in situ under reaction conditions.

Further, the hydroformylation process may be conducted at a reaction temperature from about 20° C. to about 200° C., preferably from about 50° C. to about 150° C., and more preferably from about 65° C. to about 115° C. The temperature must be sufficient for reaction to occur (which may vary with catalyst system employed), but not so high that ligand or catalyst decomposition occurs. At high temperatures (which may vary with catalyst system employed), isomerization of intermediates to undesired isomers may occur.

Of course, it is to be also understood that the hydroformylation reaction conditions employed will be governed by the type of aldehyde acid salt product desired.

The hydroformylation reactions are also conducted in the presence of water or an organic solvent for the metal-ligand complex catalyst and free ligand. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of aldehyde acid salts, one may employ aldehyde acid compounds corresponding to the aldehyde acid salt products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehyde salts include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and glyme), 1,4-butanediols and sulfolane. Suitable solvents are disclosed in U.S. Pat. No. 5,312,996. The amount of solvent employed is not critical to the subject invention and need only be that amount sufficient to solubilize the catalyst and free ligand of the hydroformylation reaction mixture to be treated. In general, the amount of solvent may range from about 5 percent by weight up to about 99 percent by weight or more based on the total weight of the hydroformylation reaction mixture starting material.

In an embodiment of the invention, the hydroformylation reaction mixture may consist of one or more liquid phases, e.g. a polar and a nonpolar phase. The reaction can be conducted in a liquid phase from which the product and/or catalyst can be separated by extraction into a separate liquid phase. A product-containing phase may also spontaneously separate during or after the reaction. Such processes are often advantageous in, for example, separating products from catalyst and/or reactants by partitioning into either phase. In addition, product selectivities dependent upon solvent properties may be increased by carrying out the reaction in that solvent. A well-known application of this technology is the aqueous-phase hydroformylation of olefins employing sulfonated phosphine ligands for the rhodium catalyst. A process carried out in aqueous solvent is particularly advantageous for the preparation of aldehyde salts because the products may be separated from the catalyst by extraction into an organic solvent. Alternatively, aldehydes which tend to undergo self-condensation reactions, are expected to be stabilized in aqueous solution as the aldehyde hydrates.

As described herein, the phosphorus-containing ligand for the rhodium hydroformylation catalyst may contain any of a number of substituents, such as cationic or anionic substituents, which will render the catalyst soluble in a polar phase, e.g. water. Optionally, a phase-transfer catalyst may be added to the reaction mixture to facilitate transport of the catalyst, reactants, or products into the desired solvent phase. The structure of the ligand or the phase-transfer catalyst is not critical and will depend on the choice of conditions, reaction solvent, and desired products.

When the catalyst is present in a multiphasic system, the catalyst may be separated from the reactants and/or products by conventional methods such as extraction or decantation. The reaction mixture itself may consist of one or more phases; alternatively, the multiphasic system may be created at the end of the reaction by for example addition of a second solvent to separate the products from the catalyst. See, for example, U.S. Pat. No. 5,180,854, the disclosure of which is incorporated herein by reference.

In an embodiment of the process of this invention, an olefin can be hydroformylated along with a pentenoic acid salt using the above-described metal-ligand complex catalysts. In such cases, an aldehyde derivative of the olefin is also produced along with the formylvaleric acid salt.

Mixtures of different olefinic starting materials can be employed, if desired, in the hydroformylation reactions. More preferably the hydroformylation reactions are especially useful for the production of formylvaleric acid salts, by hydroformylating pentenoic acid salts in the presence of alpha olefins containing from 2 to 30, preferably 4 to 20, carbon atoms, including isobutylene, and internal olefins containing from 4 to 20 carbon atoms as well as starting material mixtures of such alpha olefins and internal olefins. Commercial alpha olefins containing four or more carbon atoms may contain minor amounts of corresponding internal olefins and/or their corresponding saturated hydrocarbon and that such commercial olefins need not necessarily be purified from same prior to being hydroformylated.

Illustrative of other olefinic starting materials include alpha-olefins, internal olefins, 1,3-dienes, alkyl alkenoates, alkenyl alkanoates, alkenyl alkyl ethers, alkenols, alkenals, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, piperylene, isoprene, 2-ethyl-1-hexene, 2-octene, styrene, 3-phenyl-1-propene, 1,4-hexadiene, 1,7-octadiene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, vinyl cyclohexene, allyl ethyl ether, methyl pentenoate, 3-pentenoic acid, n-propyl-7-octenoate, pentenals, e.g., 2-pentenal, 3-pentenal and 4-pentenal; pentenols, e.g., 2-pentenol, 3-pentenol and 4-pentenol; 3-butenenitrile, 3-pentenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, iso-safrole, anethol, 4-allylanisole, indene, limonene, beta-pinene, dicyclopentadiene, cyclooctadiene, camphene, linalool, and the like. Other illustrative olefinic compounds may include, for example, p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4- propenylbenzene, phenyl vinyl ether and the like. Other olefinic compounds include substituted aryl ethylenes as described in U.S. Pat. No. 4,329,507, the disclosure of which is incorporated herein by reference.

As indicated above, it is generally preferred to carry out the hydroformylation process of this invention in a continuous manner. In general, continuous hydroformylation processes are well known in the art and may involve: (a) hydroformylating the unsaturated acid salt starting material (s) with carbon monoxide and hydrogen in a liquid homogeneous reaction mixture comprising a solvent, the metal-ligand complex catalyst, and free ligand; (b) maintaining reaction temperature and pressure conditions favorable to the hydroformylation of the unsaturated acid salt starting material(s); (c) supplying make-up quantities of the unsaturated acid salt starting material(s), carbon monoxide and hydrogen to the reaction medium as those reactants are used up; and (d) recovering the desired aldehyde salt hydroformylation product(s) in any manner desired. The continuous process can be carried out in a single pass mode, i.e., wherein the aldehyde acid salt product is removed from the liquid reaction mixture from whence a product is recovered and make-up unsaturated acid salt starting material(s), carbon monoxide and hydrogen are supplied to the liquid reaction medium for the next single pass through without recycling the unreacted unsaturated acid salt starting material(s). However, it is generally desirable to employ a continuous process that involves either a liquid and/or gas recycle procedure. Such types of recycle procedure are well known in the art and may involve the liquid recycling of the metal-ligand complex catalyst solution separated from the desired aldehyde reaction product(s), such as disclosed e.g., in U.S. Pat. No. 4,148,830 or a gas cycle procedure such as disclosed e.g., in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process.

Illustrative substituted and unsubstituted aldehyde acid salts that can be prepared by the processes of this invention include substituted and unsubstituted formylcarboxylic acid salts such as 5-formylvaleric acid salts and the like, e.g., triethylammonium 5-formylvalerate, ammonium 5-formylvalerate and octyltriethylammonium 5-formylvalerate. Illustrative of suitable substituted and unsubstituted aldehyde acid salts (including derivatives of substituted and unsubstituted aldehyde acid salts) include those permissible substituted and unsubstituted aldehyde acid salts which are described in Kirk-Othmer, Encyclopedia of Chemical Technology, Fourth Edition, 1996, the pertinent portions of which are incorporated herein by reference.

Illustrative substituted and unsubstituted epsilon caprolactam precursors that can be prepared by the processes of this invention include one or more substituted and unsubstituted 5-formylvaleric acid salts, iminocaproic acid and/or salts thereof, aminocaproic acid and/or salts thereof, caprolactam, caprolactone, imines, hemiaminals, imides, amides or amines derived from formylvaleric acid and its salts, and the corresponding dimers, trimers and oligomers. Illustrative of suitable substituted and unsubstituted epsilon caprolactam precursors (including derivatives of substituted and unsubstituted epsilon caprolactam precursors) include those permissible substituted and unsubstituted epsilon caprolactam precursors which may be described in Kirk-Othmer, Encyclopedia of Chemical Technology, Fourth Edition, 1996, the pertinent portions of which are incorporated herein by reference.

In an embodiment of this invention, the aldehyde salt mixtures may be separated from the other components of the crude reaction mixtures in which the aldehyde salt mixtures are produced by any suitable method. Suitable separation methods include, for example, solvent extraction, crystallization, distillation, vaporization, phase separation, sublimation, wiped film evaporation, falling film evaporation and the like. It may be desired to remove the aldehyde products from the crude reaction mixture as they are formed through the use of trapping agents as described in published Patent Cooperation Treaty Patent Application WO 88/08835. A method for separating the aldehyde salt mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, both incorporated herein by reference. The subsequent reductive cyclization or amination and cyclization of the aldehyde salt mixtures may be conducted without the need to separate the aldehyde salts from the other components of the crude reaction mixtures.

Particularly when conducting the process of this invention in a continuous liquid recycle mode employing an organophosphite ligand, undesirable acidic byproducts (e.g., a hydroxy alkyl phosphonic acid) may result due to reaction of the organophosphite ligand and the aldehyde over the course of the process. The formation of such byproducts undesirably lowers the concentration of the ligand. Such acids are often insoluble in the reaction mixture and such insolubility can lead to precipitation of an undesirable gelatinous byproduct and may also promote the autocatalytic formation of further acidic byproducts. The organopolyphosphite ligands used in the process of this invention have good stability against the formation of such acids. However, if this problem does occur, the liquid reaction effluent stream of a continuous liquid recycle process may be passed, prior to (or more preferably after) separation of the desired 5-formylvaleric acid salt product therefrom, through any suitable weakly basic anion exchange resin, such as a bed of amine Amberlyst® resin, e.g., Amberlyst® A-21, and the like, to remove some or all of the undesirable acidic byproducts prior to its reincorporation into the hydroformylation reactor. If desired, more than one such basic anion exchange resin bed, e.g. a series of such beds, may be employed and any such bed may be easily removed and/or replaced as required or desired. Alternatively if desired, any part or all of the acid-contaminated catalyst recycle stream may be periodically removed from the continuous recycle operation and the contaminated liquid so removed treated in the same fashion as outlined above, to eliminate or reduce the amount of acidic by-product prior to reusing the catalyst containing liquid in the hydroformylation process. Likewise, any other suitable method for removing such acidic byproducts from the hydroformylation process of this invention may be employed herein if desired such as by extraction of the acid with a weak base (e.g., sodium bicarbonate).

The processes useful in this invention may involve improving the catalyst stability of any organic solubilized rhodium-organopolyphosphite complex catalyzed, liquid recycle hydroformylation process directed to producing aldehydes from olefinic unsaturated compounds which may experience deactivation of the catalyst due to recovery of the aldehyde product by vaporization separation from a reaction product solution containing the organic solubilized rhodium-organopolyphosphite complex catalyst and aldehyde product, the improvement comprising carrying out said vaporization separation in the presence of a heterocyclic nitrogen compound. See, for example, copending U.S. patent application Ser. No. 08/756,789, filed Nov. 26, 1996, the disclosure of which is incorporated herein by reference.

The processes useful in this invention may involve improving the hydrolytic stability of the organophosphite ligand and thus catalyst stability of any organic solubilized rhodium-organophosphite ligand complex catalyzed hydroformylation process directed to producing aldehydes from olefinic unsaturated compounds, the improvement comprising treating at least a portion of an organic solubilized rhodium-organophosphite ligand complex catalyst solution derived from said process and which also contains phosphorus acidic compounds formed during the hydroformylation process, prior to (or more preferably after) separation of the desired 5-formylvaleric acid salt product therefrom, with an aqueous buffer solution in order to neutralize and remove at least some amount of said phosphorus acidic compounds from said catalyst solution, and then returning the treated catalyst solution to the hydroformylation reactor. See, for example, copending U.S. patent application Ser. Nos. 08/756,501 and 08/753,505, both filed Nov. 26, 1996, the disclosures of which are incorporated herein by reference.

In an embodiment of this invention, deactivation of metal-organopolyphosphorus ligand complex catalysts caused by an inhibiting or poisoning organomonophosphorus compound can be reversed or at least minimized by carrying out hydroformylation processes in a reaction region where the hydroformylation reaction rate is of a negative or inverse order in carbon monoxide and optionally at one or more of the following conditions: at a temperature such that the temperature difference between reaction product fluid temperature and inlet coolant temperature is sufficient to prevent and/or lessen cycling of carbon monoxide partial pressure, hydrogen partial pressure, total reaction pressure, hydroformylation reaction rate and/or temperature during said hydroformylation process; at a carbon monoxide conversion sufficient to prevent and/or lessen cycling of carbon monoxide partial pressure, hydrogen partial pressure, total reaction pressure, hydroformylation reaction rate and/or temperature during said hydroformylation process; at a hydrogen conversion sufficient to prevent and/or lessen cycling of carbon monoxide partial pressure, hydrogen partial pressure, total reaction pressure, hydroformylation reaction rate and/or temperature during said hydroformylation process; and at an olefinic unsaturated compound conversion sufficient to prevent and/or lessen cycling of carbon monoxide partial pressure, hydrogen partial pressure, total reaction pressure, hydroformylation reaction rate and/or temperature during said hydroformylation process. See, for example, copending U.S. patent application Ser. No. 08/756,499, filed Nov. 26, 1996, the disclosure of which is incorporated herein by reference.

The aldehyde acid salts described herein are useful in a variety of applications, such as the manufacture of epsilon caprolactam and the like.

The hydroformylation processes of this invention can be operated over a wide range of reaction rates (m/L/h=moles of product/liter of reaction solution/hour). Typically, the reaction rates are at least 0.01 m/L/h or higher, preferably at least 0.1 m/L/h or higher, and more preferably at least 0.5 m/L/h or higher. Higher reaction rates are generally preferred from an economic standpoint, e.g., smaller reactor size, etc.

A process for producing one or more substituted or unsubstituted epsilon caprolactams from one or more substituted or unsubstituted alkadienes is disclosed in copending U.S. patent application Ser. No. 08/839,576, filed on an even date herewith, the disclosure of which is incorporated herein by reference.

The hydroformylation processes of this invention may be carried out using, for example, a fixed bed reactor, a fluid bed reactor, or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The hydroformylation processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The hydroformylation processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation processes of this invention may be conducted in one or more steps or stages. The exact number of reaction steps or stages will be governed by the best compromise between achieving high catalyst selectivity, activity, lifetime and ease of operability, as well as the intrinsic reactivity of the starting materials in question and the stability of the starting materials and the desired reaction product to the reaction conditions.

In an embodiment, the hydroformylation processes of this invention may be carried out in a multistaged reactor such as described, for example, in copending U.S. patent application Ser. No.08/757,743, filed on Nov. 26, 1996, the disclosure of which is incorporated herein by reference. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

The substituted and unsubstituted aldehyde acid salts produced by the processes of this invention can undergo further reaction(s) to afford desired derivatives thereof. Such permissible derivatization reactions can be carried out in accordance with conventional procedures known in the art. Illustrative derivatization reactions include, for example, hydrogenation, esterification, reductive cyclization, reductive amination, cyclization, polymerization, copolymerization, amination, alkylation, dehydrogenation, reduction, acylation, condensation, oxidation, silylation and the like, including permissible combinations thereof. This invention is not intended to be limited in any manner by the permissible derivatization reactions or permissible derivatives of substituted and unsubstituted aldehyde acid salts.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

For purposes of this invention, the chemical elements are identified in accordance with the Periodic Table of the Elements reproduced in "Basic Inorganic Chemistry" by F. Albert Cotton, Geoffrey Wilkinson and Paul L. Gaus, published by John Wiley and Sons, Inc., 3rd Edition, 1995.

Certain of the following examples are provided to further illustrate this invention.

EXAMPLE 1

A 160 milliliter magnetically stirred autoclave was purged with 1:1 $H_2/CO$ and charged with a catalyst solution consisting of 0.15 mmol of dicarbonylacetylacetonato rhodium (I), 0.74 mmol of Ligand F described herein, and 30 milliliters of tetrahydrofuran. The autoclave was pressurized with 10 psig 1:1 $H_2/CO$ and heated to 85° C. A solution of the triethylammonium salt of 3-pentenoic acid was prepared by addition of 23 mmol of triethylamine to 22 mmol of 3-pentenoic acid in 2 milliliters of tetrahydrofuran. This solution was added to the autoclave by syringe and the reaction mixture pressurized to 100 psig with 1:1 $H_2/CO$. After 170 minutes of reaction at 85° C., under 100 psi 1:1 $H_2/CO$, gas chromatography analysis of the reaction products (as their free acids) provided the following results: 88% of 5-formylvaleric acid, 7% of branched formylvaleric acids, 5% of valeric acid and 1% of 2-pentenoic acid.

EXAMPLE 2

A 160 milliliter magnetically stirred autoclave was purged with 1:1 $H_2/CO$ and charged with a catalyst solution consisting of 0.14 mmol of dicarbonylacetylacetonato rhodium (I), 0.60 mmol of Ligand F described herein, and 50 milliliters of tetrahydrofuran. The autoclave was pressurized with 100 psig 1:1 $H_2/CO$ and heated to 85° C. 20 mmol of 3-pentenoic acid was added to the autoclave by syringe and the reaction mixture pressurized to 150 psig with 1:1 $H_2/CO$. After 150 minutes of reaction at 85° C. under 150 psi 1:1 $H_2/CO$, gas chromatography analysis of the reaction products provided the following results: 75% of 5-formylvaleric acid, 6% of branched formylvaleric acids, 8% of valeric acid, 5% of 2-pentenoic acid and 4% of 3-pentenoic acid.

EXAMPLE 3

A 160 milliliter magnetically stirred autoclave was purged with $N_2$ and charged with a catalyst solution consisting of 0.15 mmol of dicarbonylacetylacetonato rhodium (I), 0.73 mmol of Ligand F described herein, and 30 milliliters of tetrahydrofuran. The autoclave was pressurized to 10 psig with $N_2$ and heated to 85° C. A solution of the triethylammonium salt of 4-pentenoic acid was prepared by addition of 21 mmol of triethylamine to 22 mmol of 4-pentenoic acid in 4 milliliters of tetrahydrofuran. This solution was added to the autoclave by syringe and the reaction mixture pressurized to 100 psig with 1:1 $H_2/CO$. After 155 minutes of reaction at 85° C., under 100 psi 1:1 $H_2/CO$, gas chromatography analysis of the reaction products (as their free acids) provided the following results: 93% of 5-formylvaleric acid, 3% of branched formylvaleric acids, 4% of valeric acid and <1% of 2-pentenoic acid.

EXAMPLE 4

A 160 milliliter magnetically stirred autoclave was purged with 1:1 $H_2/CO$ and charged with a catalyst solution consisting of 0.15 mmol of dicarbonylacetylacetonato rhodium (I), 0.66 mmol of Ligand F described herein, and 50 milliliters of tetrahydrofuran. The autoclave was pressurized to 30 psig with 1:1 $H_2/CO$ and heated to 85° C. 40 mmol of 4-pentenoic acid was added to the autoclave by syringe and the reaction mixture pressurized to 120 psig with 1:1 $H_2/CO$. The reaction was maintained at 85° C. and the autoclave periodically repressurized to 120 psig. After 220 minutes of reaction at 85° C., gas chromatography analysis of the reaction products provided the following results: 77% of 5-formylvaleric acid, 6% of branched formylvaleric acids, 9% of valeric acid, 6% of 2-pentenoic acid and 2% of 3-pentenoic acid.

EXAMPLE 5

A 160 milliliter magnetically stirred autoclave was purged with 1:1 $H_2/CO$ and charged with a catalyst solution consisting of 0.14 mmol of dicarbonylacetylacetonato rhodium (I), 0.65 mmol of Ligand F described herein, 26 mmol of benzotriazole and 50 milliliters of tetrahydrofuran. The autoclave was pressurized with 75 psig 1:1 $H_2/CO$ and heated to 85° C. 20 mmol of 3-pentenoic acid was added to the autoclave by syringe and the reaction mixture pressurized to 150 psig with 1:1 $H_2/CO$. After 105 minutes of reaction at 85° C., under 150 psi 1:1 $H_2/CO$, gas chromatography analysis of the reaction products (as their free acids) provided the following results: 73% of 5-formylvaleric acid, 8% of branched formylvaleric acids, 7% of valeric acid, 7% of 2-pentenoic acid and 4% of 3-pentenoic acid.

EXAMPLE 6

A 160 milliliter magnetically stirred autoclave was purged with $N_2$ and charged with a catalyst solution consisting of 0.15 mmol of dicarbonylacetylacetonato rhodium (I), 0.73 mmol of Ligand F described herein, and 28 milliliters of tetrahydrofuran. The autoclave was pressurized with 15 psig $N_2$ and heated to 85° C. A solution of the triethylammonium salt of trans-2-pentenoic acid was prepared by addition of 20 mmol of triethylamine to 24 mmol of trans-2-pentenoic acid in 4 milliliters of tetrahydrofuran. This solution was added to the reactor by syringe and the reaction mixture pressurized to 100 psig with 1:1 $H_2/CO$. After 145 minutes of reaction at 85° C. under 100 psi 1:1 $H_2/CO$, gas chromatography analysis of the reaction products (as their free acids) provided the following results: 9% of 5-formylvaleric acid, 1% of branched formylvaleric acids, 68% of valeric acid, 21% of 2-pentenoic acid and 1% of 3-pentenoic acid.

EXAMPLE 7

A 160 milliliter magnetically stirred autoclave was purged with $N_2$ and charged with a catalyst solution consisting of 0.15 mmol of dicarbonylacetylacetonato rhodium (I), 0.74 mmol of Ligand F described herein, and 30 milliliters of tetrahydrofuran. The autoclave was pressurized with 15 psig $N_2$ and heated to 85° C. 20 mmol of trans-2-pentenoic acid was added to the reactor by syringe and the reaction mixture pressurized to 100 psig with 1:1 $H_2/CO$. After 150 minutes of reaction at 85° C. under 100 psi 1:1 $H_2/CO$, gas chromatography analysis of the reaction products provided the following results: 5% of 5-formylvaleric acid, 2% of branched formylvaleric acids, 76% of valeric acid, 16% of 2-pentenoic acid and 1% of 3-pentenoic acid.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for producing one or more substituted or unsubstituted aldehyde acid salts and/or one or more substituted or unsubstituted epsilon caprolactam precursors which comprises subjecting one or more substituted or unsubstituted unsaturated acid salts to hydroformylation in the presence of a metal-ligand complex catalyst to produce said one or more substituted or unsubstituted aldehyde acid salts and/or one or more substituted or unsubstituted epsilon caprolactam precursors.

2. The process of claim 1 wherein the substituted or unsubstituted unsaturated acid salt comprises 3-pentenoic acid salt, 4-pentenoic acid salt and/or 2-pentenoic acid salt and the substituted or unsubstituted aldehyde acid salt comprises 5-formylvaleric acid salt.

3. The process of claim 1 wherein said metal-ligand complex catalyst comprises a metal selected from a Group 8, 9 and 10 metal complexed with an organophosphorus ligand selected from a mono-, di-, tri- and poly (orgnophosphine) ligand.

4. The process of claim 1 wherein said metal-ligand complex catalyst comprises a metal selected from a Group 8, 9 and 10 metal complexed with an organophosphorus ligand selected from:

(i) a triorganophosphine ligand represented by the formula:

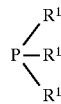

wherein each $R^1$ is the same or different and is a substituted or unsubstituted monovalent hydrocarbon radical;

(ii) a monoorganophosphite represented by the formula:

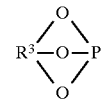

wherein $R^3$ represents a substituted or unsubstituted trivalent hydrocarbon radical containing from 4 to 40 carbon atoms or greater;

(iii) a diorganophosphite represented by the formula:

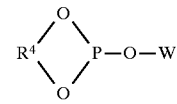

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

wherein each $R^8$ is the same or different and is a substituted or unsubstituted monovalent hydrocarbon radical; and (v) an organopolyphosphite containing two or more tertiary (trivalent) phosphorus atoms represented by the formula:

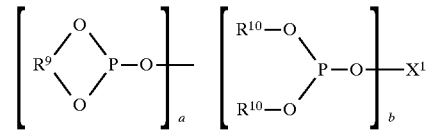

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

5. The process of claim 1 wherein said metal-ligand complex catalyst comprises a metal selected from a Group 8, 9 and 10 metal complexed with an organophosphorus ligand having the formula:

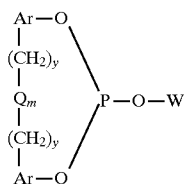

wherein W represents a substituted or unsubstituted monovalent hydrocarbon radical containing from 1 to 18 carbon atoms or greater, each Ar is the same or different and represents a substituted or unsubstituted aryl radical, each y is the same or different and is a value of 0 or 1, Q represents a divalent bridging group selected from —C($R^5$)$_2$—, —O—, —S—, —N$R^6$—, Si($R^7$)$_2$— and —CO—, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

6. The process of claim 1 wherein said metal-ligand complex catalyst comprises a metal selected from a Group 8, 9 and 10 metal complexed with an organophosphorus ligand having the formula selected from:

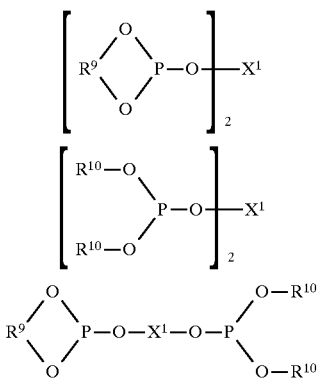

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, and each $R^{10}$ is the same or different and is a substituted or unsubstituted monovalent hydrocarbon radical containing from 1 to 24 carbon atoms.

7. The process of claim 1 wherein said metal-ligand complex catalyst comprises a metal selected from a Group 8, 9 and 10 metal complexed with an organophosphorus ligand having the formula selected from:

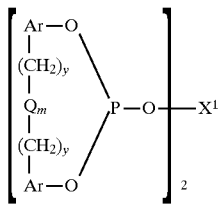

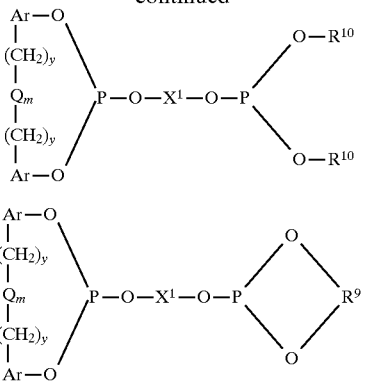

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, each Ar is the same or different and represents a substituted or unsubstituted aryl radical, each y is the same or different and is a value of 0 or 1, Q represents a divalent bridging group selected from —C($R^5$)$_2$—, —O—, —S—, —N$R^6$—, Si($R^7$)$_2$— and —CO—, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

8. The process of claim 1 wherein the reaction is conducted in the presence of an olefin and an aldehyde of the olefin is also produced.

9. The process of claim 1 which is conducted at a temperature from about 50° C. to 150° C. and at a total pressure from about 200 psig to about 1000 psig.

10. A process for producing a batchwise or continuously generated reaction mixture comprising:
   (1) one or more substituted or unsubstituted 5-formylvaleric acid salts and/or one or more substituted or unsubstituted epsilon caprolactam precursors;
   (2) optionally one or more substituted or unsubstituted 4-formylvaleric acid salts and/or 3-formylvaleric acid salts;
   (3) optionally one or more substituted or unsubstituted valeric acid salts; and
   (4) one or more substituted or unsubstituted pentenoic acid salts;
      wherein the weight ratio of component (1) to the sum of components (2) and (3) is greater than about 0.1; and the weight ratio of component (4) to the sum of components (1), (2) and (3) is about 0 to about 100; which process comprises subjecting one or more substituted or unsubstituted pentenoic acid salts to hydroformylation in the presence of a metal-ligand complex catalyst to produce said batchwise or continuously generated reaction mixture.

11. A process for producing a reaction mixture comprising one or more substituted or unsubstituted aldehyde acid salts and/or one or more substituted or unsubstituted epsilon caprolactam precursors which process comprises subjecting one or more substituted or unsubstituted unsaturated acid salts to hydroformylation in the presence of a metal-ligand complex catalyst to produce said reaction mixture comprising one or more substituted or unsubstituted aldehyde acid salts and/or one or more substituted or unsubstituted epsilon caprolactam precursors.

12. A batchwise or continuously generated reaction mixture comprising:
(1) one or more substituted or unsubstituted 5-formylvaleric acid salts and/or one or more substituted or unsubstituted epsilon caprolactam precursors;
(2) optionally one or more substituted or unsubstituted 4-formylvaleric acid salts and/or 3-formylvaleric acid salts;
(3) optionally one or more substituted or unsubstituted valeric acid salts; and
(4) one or more substituted or unsubstituted pentenoic acid salts;
wherein the weight ratio of component (1) to the sum of components (2) and (3) is greater than about 0.1; and the weight ratio of component (4) to the sum of components (1), (2) and (3) is about 0 to about 100.

13. A reaction mixture comprising one or more substituted or unsubstituted aldehyde acid salts and/or one or more substituted or unsubstituted epsilon caprolactam precursors in which said reaction mixture is prepared by a process which comprises subjecting one or more substituted or unsubstituted unsaturated acid salts to hydroformylation in the presence of a metal-ligand complex catalyst to produce said reaction mixture comprising one or more substituted or unsubstituted aldehyde acid salts and/or one or more substituted or unsubstituted epsilon caprolactam precursors.

14. The reaction mixture of claim 13 in which the process comprises derivatizing the one or more substituted or unsubstituted aldehyde acid salts.

15. The reaction mixture of claim 14 which the derivatizing reaction comprises hydrogenation, esterification, reductive cyclization, reductive amination, cyclization, polymerization, copolymerization, amination, alkylation, dehydrogenation, reduction, acylation, condensation, oxidation, silylation and permissible combinations thereof.

* * * * *